(12) United States Patent
Veldman et al.

(10) Patent No.: US 7,931,676 B2
(45) Date of Patent: Apr. 26, 2011

(54) VERTEBRAL STABILIZER

(75) Inventors: Michael S. Veldman, Memphis, TN (US); Jonathan Dewey, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 756 days.

(21) Appl. No.: 11/624,415

(22) Filed: Jan. 18, 2007

(65) Prior Publication Data

US 2008/0177318 A1 Jul. 24, 2008

(51) Int. Cl.
*A61B 17/70* (2006.01)
(52) U.S. Cl. ......... 606/261; 606/246; 606/270; 606/308
(58) Field of Classification Search .............. 606/60, 606/246, 250–279
See application file for complete search history.

(56) References Cited

U.S. PATENT DOCUMENTS

| | | | |
|---|---|---|---|
| 3,997,138 A | 12/1976 | Crock et al. | |
| 4,386,603 A | 6/1983 | Mayfield | |
| 4,573,454 A | 3/1986 | Hoffman | |
| 4,686,970 A | 8/1987 | Dove et al. | |
| 4,697,582 A * | 10/1987 | William | 606/254 |
| 4,743,260 A | 5/1988 | Burton | |
| 4,771,767 A | 9/1988 | Steffee | |
| 5,092,866 A | 3/1992 | Breard et al. | |
| 5,180,393 A | 1/1993 | Commarmond | |
| 5,217,461 A | 6/1993 | Asher et al. | |
| 5,282,863 A | 2/1994 | Burton | |
| 5,330,472 A | 7/1994 | Metz-Stavenhagen | |
| 5,375,823 A | 12/1994 | Navas | |
| 5,387,213 A | 2/1995 | Breard et al. | |
| 5,413,576 A | 5/1995 | Rivard | |
| 5,415,661 A | 5/1995 | Holmes | |
| 5,425,732 A | 6/1995 | Ulrich | |
| 5,456,722 A | 10/1995 | McLeod et al. | |
| 5,480,401 A | 1/1996 | Navas | |
| 5,540,688 A | 7/1996 | Navas | |
| 5,562,660 A | 10/1996 | Grob | |
| 5,562,737 A | 10/1996 | Graf | |
| 5,575,819 A | 11/1996 | Amis | |
| 5,593,408 A | 1/1997 | Gayet et al. | |
| 5,667,506 A | 9/1997 | Sutterlin | |
| 5,672,175 A | 9/1997 | Martin | |
| 5,681,311 A | 10/1997 | Foley et al. | |
| 5,704,936 A | 1/1998 | Mazel | |
| 5,733,284 A | 3/1998 | Martin | |
| 5,738,685 A * | 4/1998 | Halm et al. | 606/270 |
| 5,879,351 A * | 3/1999 | Viart | 606/264 |

(Continued)

FOREIGN PATENT DOCUMENTS

DE 9112466 12/1991

(Continued)

OTHER PUBLICATIONS

Unpublished U.S. Appl. No. 11/413,448, filed Apr. 28, 2006 titled Vertebral Stabilizer.
Unpublished U.S. Appl. No. 11/469,354, filed Aug. 31, 2006 titled Polymer Rods for Spinal Applications.
Unpublished U.S. Appl. No. 11/563,594, filed Nov. 27, 2006 titled Vertebral Stabilizer Having Adjustable Rigidity.

(Continued)

*Primary Examiner* — Eduardo C Robert
*Assistant Examiner* — Jerry Cumberledge (57) ABSTRACT

A bio-compatible stabilization system includes one or more inserters and a spinal stabilization connector for traversing a space between one or more bony structures. The stabilization system is designed to reduce or eliminate stress shielding effects while functioning as a tension band. The stabilization rod is shaped to define a fixed number of discrete positions of orientation.

21 Claims, 7 Drawing Sheets

U.S. PATENT DOCUMENTS

| | | | |
|---|---|---|---|
| RE36,221 E | 6/1999 | Breard et al. | |
| 5,951,553 A | 9/1999 | Betz et al. | |
| 5,961,516 A | 10/1999 | Graf | |
| 6,099,528 A | 8/2000 | Saurat | |
| 6,102,912 A | 8/2000 | Cazin et al. | |
| 6,183,473 B1 | 2/2001 | Ashman | |
| 6,210,413 B1 | 4/2001 | Justis et al. | |
| 6,241,730 B1 | 6/2001 | Alby | |
| 6,267,764 B1 | 7/2001 | Elberg | |
| 6,280,442 B1 | 8/2001 | Barker et al. | |
| 6,287,308 B1 | 9/2001 | Betz et al. | |
| 6,293,949 B1 | 9/2001 | Justis et al. | |
| 6,296,642 B1 | 10/2001 | Morrison et al. | |
| 6,296,643 B1 | 10/2001 | Hopf et al. | |
| 6,299,613 B1 | 10/2001 | Ogilvie et al. | |
| 6,325,805 B1 | 12/2001 | Ogilvie et al. | |
| 6,436,099 B1 | 8/2002 | Drewry et al. | |
| 6,461,359 B1 | 10/2002 | Tribus et al. | |
| 6,485,492 B1* | 11/2002 | Halm et al. | 606/267 |
| 6,488,682 B2 | 12/2002 | Kikuchi et al. | |
| 6,488,683 B2 | 12/2002 | Lieberman | |
| 6,551,320 B2 | 4/2003 | Lieberman | |
| 6,554,831 B1 | 4/2003 | Rivard et al. | |
| 6,616,669 B2 | 9/2003 | Ogilvie et al. | |
| 6,623,484 B2 | 9/2003 | Betz et al. | |
| 6,626,904 B1 | 9/2003 | Jammet et al. | |
| 6,645,211 B2 | 11/2003 | Magana | |
| 6,730,092 B2 | 5/2004 | Songer | |
| 6,740,086 B2 | 5/2004 | Richelsoph | |
| 6,746,450 B1 | 6/2004 | Wall et al. | |
| 6,749,614 B2 | 6/2004 | Teitelbaum et al. | |
| 6,752,831 B2 | 6/2004 | Sybert et al. | |
| 6,758,862 B2 | 7/2004 | Berry et al. | |
| 6,761,719 B2 | 7/2004 | Justis et al. | |
| 6,773,437 B2 | 8/2004 | Ogilvie et al. | |
| 6,783,527 B2 | 8/2004 | Drewry et al. | |
| 6,802,844 B2 | 10/2004 | Ferree | |
| 6,875,212 B2 | 4/2005 | Shaolian et al. | |
| 6,899,713 B2 | 5/2005 | Shaolian et al. | |
| 6,902,565 B2 | 6/2005 | Berger et al. | |
| 6,921,403 B2 | 7/2005 | Cragg et al. | |
| 7,083,621 B2 | 8/2006 | Shaolian et al. | |
| 7,632,292 B2* | 12/2009 | Sengupta et al. | 606/257 |
| 2002/0091388 A1* | 7/2002 | Nohara et al. | 606/61 |
| 2002/0116001 A1* | 8/2002 | Schafer et al. | 606/61 |
| 2002/0133155 A1 | 9/2002 | Ferree | |
| 2002/0143329 A1 | 10/2002 | Serhan et al. | |
| 2003/0009226 A1 | 1/2003 | Graf | |
| 2003/0023241 A1 | 1/2003 | Drewry et al. | |
| 2003/0055427 A1 | 3/2003 | Graf | |
| 2003/0088251 A1 | 5/2003 | Braun et al. | |
| 2003/0093078 A1 | 5/2003 | Ritland | |
| 2003/0100897 A1 | 5/2003 | Metz-Stavenhagen | |
| 2003/0109880 A1 | 6/2003 | Shirado et al. | |
| 2003/0171749 A1 | 9/2003 | Le Couedic et al. | |
| 2003/0191470 A1* | 10/2003 | Ritland | 606/61 |
| 2003/0220642 A1 | 11/2003 | Freudiger | |
| 2003/0220643 A1 | 11/2003 | Ferree | |
| 2003/0229347 A1* | 12/2003 | Sherman et al. | 606/61 |
| 2004/0002708 A1 | 1/2004 | Ritland | |
| 2004/0049189 A1* | 3/2004 | Le Couedic et al. | 606/61 |
| 2004/0073215 A1 | 4/2004 | Carli | |
| 2004/0082954 A1 | 4/2004 | Teitelbaum et al. | |
| 2004/0092934 A1 | 5/2004 | Howland | |
| 2004/0138666 A1 | 7/2004 | Molz, IV et al. | |
| 2004/0147928 A1 | 7/2004 | Landry et al. | |
| 2004/0172025 A1 | 9/2004 | Drewry et al. | |
| 2004/0215341 A1 | 10/2004 | Sybert et al. | |
| 2004/0220569 A1 | 11/2004 | Wall et al. | |
| 2004/0225289 A1 | 11/2004 | Biedermann et al. | |
| 2004/0236327 A1 | 11/2004 | Paul et al. | |
| 2004/0236328 A1 | 11/2004 | Paul et al. | |
| 2004/0236329 A1 | 11/2004 | Panjabi | |
| 2005/0038432 A1 | 2/2005 | Shaolian et al. | |
| 2005/0065515 A1 | 3/2005 | Jahng | |
| 2005/0065516 A1 | 3/2005 | Jahng | |
| 2005/0070908 A1 | 3/2005 | Cragg | |
| 2005/0085812 A1 | 4/2005 | Sherman et al. | |
| 2005/0085814 A1 | 4/2005 | Sherman et al. | |
| 2005/0085815 A1 | 4/2005 | Harms et al. | |
| 2005/0090822 A1 | 4/2005 | DiPoto | |
| 2005/0102028 A1 | 5/2005 | Arnin et al. | |
| 2005/0124991 A1 | 6/2005 | Jahng | |
| 2005/0131405 A1 | 6/2005 | Molz, IV et al. | |
| 2005/0143737 A1 | 6/2005 | Pafford et al. | |
| 2005/0143823 A1 | 6/2005 | Boyd et al. | |
| 2005/0149020 A1 | 7/2005 | Jahng | |
| 2005/0154390 A1 | 7/2005 | Biedermann et al. | |
| 2005/0171539 A1 | 8/2005 | Braun et al. | |
| 2005/0171540 A1 | 8/2005 | Lim et al. | |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0182401 A1 | 8/2005 | Timm et al. | |
| 2005/0182409 A1 | 8/2005 | Callahan et al. | |
| 2005/0192581 A1 | 9/2005 | Molz et al. | |
| 2005/0197660 A1* | 9/2005 | Haid et al. | 606/61 |
| 2005/0203511 A1 | 9/2005 | Wilson-MacDonald et al. | |
| 2005/0203513 A1 | 9/2005 | Jahng et al. | |
| 2005/0203514 A1* | 9/2005 | Jahng et al. | 606/61 |
| 2005/0203516 A1 | 9/2005 | Biedermann et al. | |
| 2005/0203517 A1 | 9/2005 | Jahng et al. | |
| 2005/0203518 A1* | 9/2005 | Biedermann et al. | 606/61 |
| 2005/0203519 A1 | 9/2005 | Harms et al. | |
| 2005/0209694 A1 | 9/2005 | Loeb | |
| 2005/0216004 A1 | 9/2005 | Schwab | |
| 2005/0222569 A1 | 10/2005 | Panjabi | |
| 2005/0228381 A1 | 10/2005 | Kirschman | |
| 2005/0240183 A1 | 10/2005 | Vaughan | |
| 2005/0245930 A1 | 11/2005 | Timm et al. | |
| 2005/0261682 A1 | 11/2005 | Ferree | |
| 2005/0261685 A1 | 11/2005 | Fortin et al. | |
| 2005/0261686 A1 | 11/2005 | Paul | |
| 2005/0267470 A1 | 12/2005 | McBride | |
| 2005/0267473 A1 | 12/2005 | Vaughan | |
| 2005/0273099 A1* | 12/2005 | Baccelli et al. | 606/61 |
| 2005/0277920 A1 | 12/2005 | Slivka et al. | |
| 2005/0277922 A1 | 12/2005 | Trieu et al. | |
| 2005/0277926 A1 | 12/2005 | Farris | |
| 2005/0277932 A1 | 12/2005 | Farris | |
| 2006/0064092 A1* | 3/2006 | Howland | 606/61 |
| 2006/0217719 A1* | 9/2006 | Albert et al. | 606/61 |
| 2006/0247638 A1* | 11/2006 | Trieu et al. | 606/69 |
| 2007/0173828 A1* | 7/2007 | Firkins et al. | 606/61 |
| 2007/0191841 A1* | 8/2007 | Justis et al. | 606/61 |
| 2007/0213720 A1* | 9/2007 | Gordon et al. | 606/61 |
| 2007/0270819 A1* | 11/2007 | Justis et al. | 606/61 |
| 2008/0086130 A1* | 4/2008 | Lake et al. | 606/61 |

FOREIGN PATENT DOCUMENTS

| | | |
|---|---|---|
| EP | 0576379 A1 | 12/1993 |
| EP | 0667127 | 8/1995 |
| EP | 0669109 | 8/1995 |
| EP | 0677277 | 10/1995 |
| EP | 0820731 | 1/1998 |
| EP | 1281361 | 5/2003 |
| EP | 1388323 A1 | 2/2004 |
| FR | 2735351 | 12/1996 |
| FR | 2799949 | 4/2001 |
| WO | WO 95/19149 | 1/1996 |
| WO | WO 01/45576 | 9/2002 |
| WO | WO 02/102259 | 12/2002 |
| WO | WO 03/003901 | 1/2003 |
| WO | WO 03/003902 | 1/2003 |
| WO | WO 2005/087121 | 9/2005 |

OTHER PUBLICATIONS

European patent Office, International Searching Authority, Notification of Transmittal of the International Search Report and the Written Opinion of the International Searching Authority or the Declaration, International Application No. PCT/US20007/065947, Sep. 5, 2007, 2 pages.

* cited by examiner

VERTEBRAL STABILIZER

BACKGROUND

Severe back pain and nerve damage may be caused by injured, degraded, or diseased spinal joints and particularly, spinal discs. Current methods of treating these damaged spinal discs may include vertebral fusion, nucleus replacements, or motion preservation disc prostheses. Other treatment methods include spinal stabilization implants whereby a stabilization connector is secured to a pair of vertebral members spaced from one another. Some stabilization connectors are constructed to flex in a certain orientation or plane yet block or restrict movement in another plane. In this regard, determining the proper orientation of the connector relative to spinal joints greatly affects the effectiveness of the connector as a spinal stabilizer.

One exemplary connector is a spinal stabilization rod. Conventionally, these rods, which may be straight or pre-bent to have desired curvature, have a circular cross-section. The shape of the spinal stabilization rod has typically been applauded as allowing the surgeon a great degree of freedom in orientating the rod relative to a vertebral member. Notwithstanding this advantage, increasingly there is a desire for the rod to positionable at one of a number of discrete orientations. That is, stabilization rods can be constructed to provide a desired performance when placed in a specific orientation. It is difficult to achieve a specific orientation with conventional rods because the shape of conventional rods results in indefinitely defined possible orientations.

Moreover, a set screw is often used to secure the spinal stabilization rod in the rod-receiving channel of a receiver. The set screw typically has a planar surface that interfaces with the outer, and curved, surface of the stabilization rod. As a result, the set screw tangentially seats against the round stabilization rod. This tangential seating can result in focalized or poorly distributed contact forces.

Therefore, it would be desirable to have a spinal stabilization connector that presents discrete orientations at which the connector can be oriented. It would also be desirable to have a spinal stabilization connector that presents a relatively planar surface for engagement with the planar surface of a set screw used to secure the connector in a receiver so that contact forces are more effectively distributed.

SUMMARY

In one aspect of the present disclosure, a spinal stabilizing system is presented having a spinal stabilization connector designed to traverse a space between a pair of vertebral members. The spinal stabilization connector is constructed to have first and second ends shaped to define a plurality of discrete positions relative to the vertebral members. The spinal stabilization connector further has a body connected to the first and second ends, and a curved portion extending between the first and second ends.

In another aspect, the present disclosure includes a spinal stabilizing kit. The kit has a pair of receivers, a pair of bone-engaging screws, a spinal stabilization connector, and a pair of locking screws. Each bone-engaging screw is retainable by a receiver and drivingly engageable with a bony structure. The spinal stabilization connector has a curved potion and first and second ends spaced from one another by the curved portion. The first and second ends are shaped to define a discrete number of positions at which the spinal stabilization connector may be retained by the pair of receivers. Each locking screw is designed to lock the spinal stabilization connector in a receiver.

According to another aspect of the present disclosure, a surgical method is presented for stabilizing a spinal joint with a spinal stabilizing system that includes a spinal stabilization connector having a curved portion that can be oriented at one of a plurality of discrete orientation positions relative to the spinal joint. The method includes fastening a first receiver to a first vertebral member and determining a desired orientation of the curved portion of the spinal stabilization connector relative to the vertebral member. The method further includes rotating the spinal stabilization connector to the discrete orientation position that corresponds to the desired orientation of the spinal stabilization connector and securing a first end of the spinal stabilization connector to the first receiver. A second receiver is fastened to a second vertebral member spaced from the first vertebral member. A second end of the spinal stabilization connector is then secured to the second receiver.

According to a further aspect of the present disclosure, an implant for stabilizing bony structures is presented. The implant has a first boss and a second boss laterally spaced from the first boss. A ribbon member extends between the first boss and the second boss along a plane different from that of the first and the second bosses. Moreover, the ribbon member has a length sufficient to traverse a space between at least two bony structures.

These and other aspects, forms, objects, features, and benefits of the present invention will become apparent from the following detailed drawings and descriptions.

BRIEF DESCRIPTION OF THE DRAWINGS

FIG. 9b is a top view of that illustrated in FIG. 9a.

DETAILED DESCRIPTION

The present disclosure relates generally to the field of orthopedic surgery, and more particularly to systems and methods for stabilizing a spinal joint. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Figure 1:
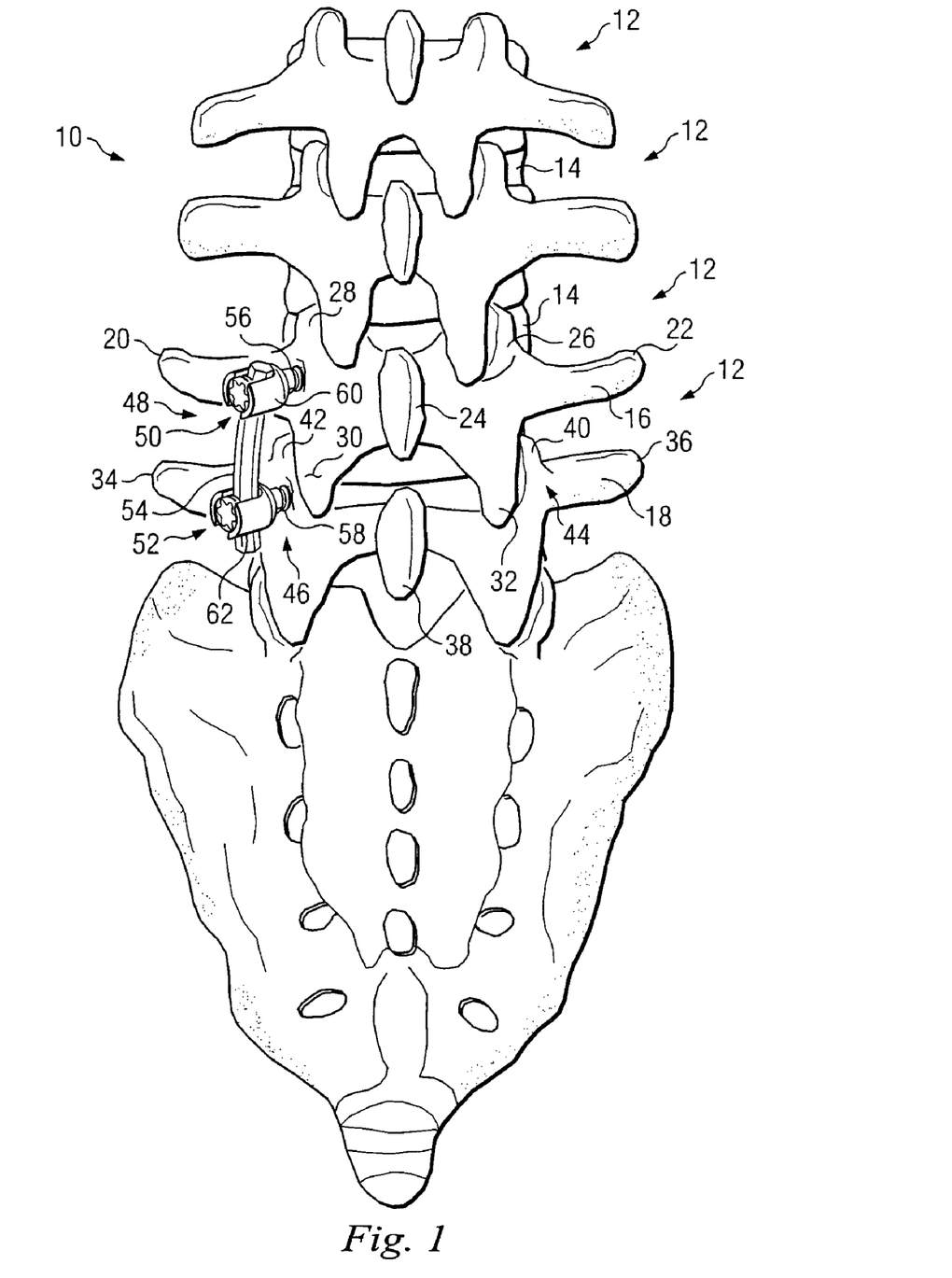
FIG. 1 is a pictorial representation of a vertebral column with a vertebral stabilizing system according to one embodiment of the present disclosure.
Figure 2:
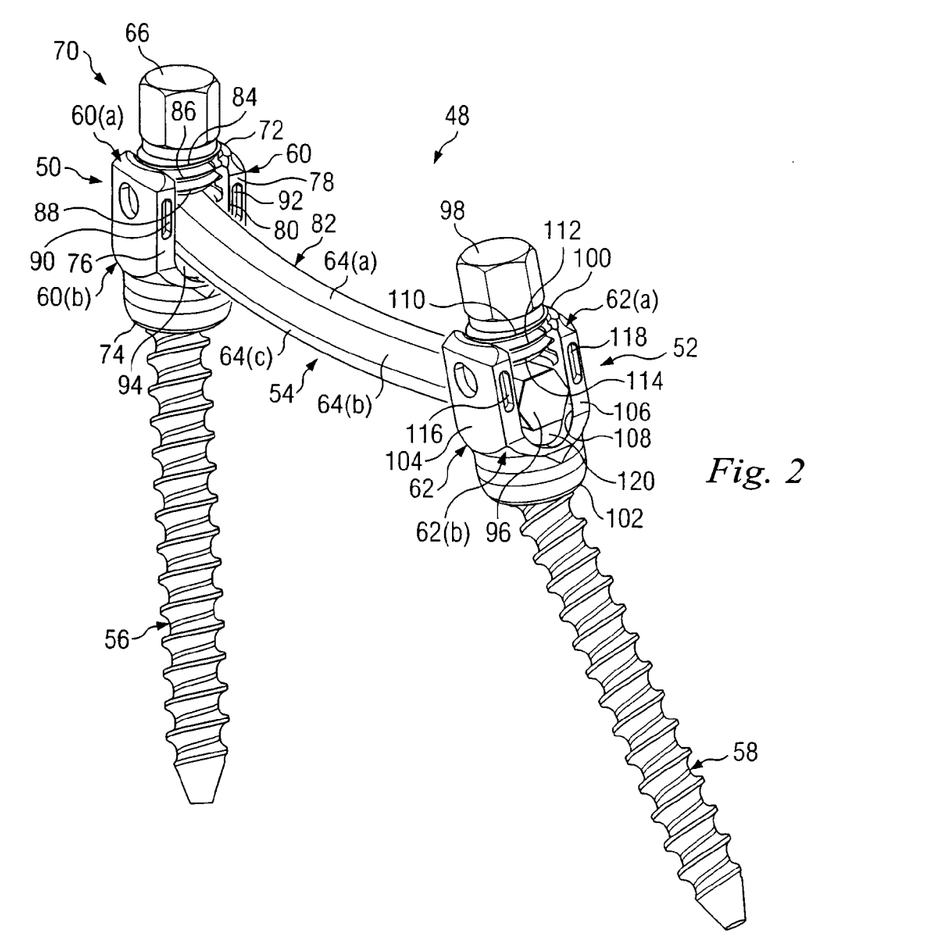
FIG. 2 is a perspective view of the vertebral stabilizing system according to one embodiment of the present disclosure.

Referring to FIGS. 1-2, the numeral 10 refers to a spinal column having a series of vertebral joints 12, each including an intervertebral disc 14. One of the vertebral joints 12 will be described further with reference to adjacent vertebrae 16, 18. The vertebra 16 includes transverse processes 20, 22, a spinous process 24, superior articular processes 26, 28, and inferior articular processes 30, 32. Similarly, the vertebra 18 includes transverse processes 34, 36, a spinous process 38, superior articular processes 40, 42, and inferior articular processes (not labeled). Although the illustration of FIG. 1 generally depicts the vertebral joint 12 as a lumbar vertebral joint, it is understood that the devices, systems, and methods of this disclosure may also be applied to all regions of the vertebral column, including the cervical and thoracic regions. Furthermore, the devices, systems, and methods of this disclosure may be used in non-spinal orthopedic applications.

A facet joint 44 is formed, in part, by the adjacent articular processes 32, 40. Likewise, another facet joint 46 is formed, in part, by the adjacent articular processes 30, 42. Facet joints also may be referred to as zygapophyseal joints. A healthy facet joint includes a facet capsule extending between the adjacent articular processes. The facet capsule comprises cartilage and synovial fluid to permit the articulating surfaces of the articular processes to remain lubricated and glide over one another. The type of motion permitted by the facet joints is dependent on the region of the vertebral column. For example, in a healthy lumbar region, the facet joints limit rotational motion but permit greater freedom for flexion, extension, and lateral bending motions. By contrast, in a healthy cervical region of the vertebral column, the facet joints permit rotational motion as well as flexion, extension, and lateral bending motions. As the facet joint deteriorates, the facet capsule may become compressed and worn, losing its ability to provide a smooth, lubricated interface between the articular surfaces of the articular processes. This may cause pain and limit motion at the affected joint. Facet joint deterioration may also cause inflammation and enlargement of the facet joint which may, in turn, contribute to spinal stenosis. Removal of an afflicted articular process may result in abnormal motions and loading on the remaining components of the joint. The embodiments described below may be used to stabilize a deteriorated facet joint while still allowing some level of natural motion.

Injury, disease, and deterioration of the intervertebral disc 14 may also cause pain and limit motion. In a healthy intervertebral joint, the intervertebral disc permits rotation, lateral bending, flexion, and extension motions. As the intervertebral joint deteriorates, the intervertebral disc may become compressed, displaced, or herniated, resulting in excess pressure in other areas of the spine, particularly the posterior bony elements of the afflicted vertebrae. This deterioration may lead to spinal stenosis. In one application, the embodiments described below may restore more natural spacing to the posterior bony elements of the vertebrae, decompress an intervertebral disc, and/or may relieve spinal stenosis. Referring still to FIGS. 1-2, in one embodiment, a vertebral stabilizing system 48 may be used to provide support to the vertebrae 16, 18, at least partially decompress the disc 14 and the facet joint 46, and/or relieve stenosis.

Connected at each end to vertebral fasteners 50, 52, a spinal stabilization connector 54 may provide compressive support and load distribution, providing relief to the intervertebral disc 14. In addition, the spinal stabilization connector 54 may dampen the forces on the intervertebral disc 14 and facet joint 46 during motion such as flexion. Because the spinal stabilization connector 54 is securely connected to the vertebral fasteners 50, 52, the spinal stabilization connector 54 also provides relief in tension/extension. Accordingly, during bending or in extension, the spinal stabilization connector 54 may assist in providing a flexible dampening force to limit the chance of overcompression or overextension when muscles are weak. In addition, the spinal stabilization connector 54 allows at least some torsional movement of the vertebra 16 relative to the vertebra 18. In one exemplary embodiment, the fasteners 50, 52 include a pedicle screw 56, 58 that together with receivers 60, 62 secure the spinal stabilization connector 54 in place. Such an exemplary fastener is described in U.S. Pat. No. 6,280,442, the disclosure of which is incorporated herein by reference.

Referring now to FIG. 2, the spinal stabilizing system 48 is shown as having a spinal stabilization connector 54 with a hexagonal cross-section. In this regard, the spinal stabilization connector 54 is defined by six sidewalls 64(a), 64(b), 64(c), 64(d), 64(e), and 64(f) that, in the illustrated example, run along the entire length of the spinal stabilization connector. Only sidewalls 64(a), 64(b), and 64(c) are viewable in FIG. 2. Each end of the spinal stabilization connector, as described with respect to FIG. 1, is retained in a vertebral fastener 50, 52.

Vertebral fastener 50 includes a receiver 60, pedicle screw 56, and a locking screw or cap 66. More particularly, receiver 60 defines an upper opening portion 60(a) and a lower opening portion 60(b), which collectively form a single opening (not numbered) that extends through the receiver 60 from an upper aperture (shown occupied by locking screw 66) in top end 72 and a lower aperture (shown occupied by pedicle screw 56) in bottom end 74. Although not shown, the bottom end 74 includes an annular groove that is sized to receive a retaining ring (not shown) against which the head (not shown) of the pedicle screw 56 seats.

Receiver 60 includes a pair of upright branches 76, 78 that collectively define a U-shaped channel 80 transverse to the single opening defined longitudinally through the receiver. Moreover, the U-shaped channel 80 communicates with upper opening portion 60(a) and lower opening portion 60(b). The U-shaped channel 80 is sized to receive the distal end 82 of spinal stabilization connector 54.

Locking cap 66 has a threaded body 84 that includes a series of threads that are compatible with internal threads (not shown) formed along the interior walls 86, 88 of branches 76, 78, respectively. In one embodiment, the internal threads of branches 76, 78 are reverse angle threads, such as disclosed in U.S. Pat. No. 6,296,242, the disclosure of which is incorporated herein by reference. It is understood, however, that the present disclosure is applicable with vertebral fasteners having other thread orientations. The branches 76, 78 also have indentations or holes 90, 92 that allow a surgeon to grip the receiver 60 with an appropriate gripping tool (not shown).

Vertebral fastener 50 also has a crown member 94 shaped to accommodate the head of pedicle screw 56. One exemplary crown member is more fully described in U.S. Pat. No. 6,280,442, the disclosure of which is incorporated herein by reference. Crown member 94 is constructed to fit within the lower opening portion 60(*b*) and compresses against the head of the pedicle screw when the spinal stabilization connector 54 is secured within U-shaped channel 80.

More particularly, crown member 94 and pedicle screw 56 are retained within the receiver 60 by inserting the crown member 94 and the head of the pedicle screw 56 through the lower aperture in bottom end 74. The retaining ring is then positioned within the annual groove defined in the bottom end 74 of the receiver to prevent the crown member 94 and pedicle screw 56 from translating through the lower aperture. A hole (not shown) formed in the crown member 94 allows a surgeon to engage a driving tool with a corresponding printed surface (not shown) of the pedicle screw head. In this regard, once a hole is appropriately prepared in a vertebral member, the pedicle screw can be threaded into the vertebral member. It is understood that the present disclosure is applicable with vertebral fasteners having configurations different from the vertebral fasteners described herein.

Following insertion of the pedicle screw 56 into the vertebral member, the spinal stabilization connector 54 is placed in the U-shaped channel 80 and in contact with the top surface of crown member 94. Locking screw 66 or other compression member is then threaded into corresponding threads of the receiver 60 and into contact with the spinal stabilization connector 54. As the locking screw 66 is driven into contact with the spinal stabilization connector 54, the spinal stabilization connector 54 is forced downward against the crown member 94 which then compresses against the head of the pedicle screw 56. It is understood that the present disclosure is applicable with other known or to be developed locking configurations.

Once the spinal stabilization connector 54 is secured by fastener 50, the proximal end 96 of the spinal stabilization connector 54 is secured to fastener 52. Fastener 52 is similar in design to fastener 50 described above. Specifically, vertebral fastener 52 includes receiver 62, pedicle screw 56, and a locking screw or cap 98. Receiver 62 defines an upper opening portion 62(*a*) and a lower opening portion 62(*b*), which collectively form a single opening (not numbered) that extends through the receiver 62 from an upper aperture (shown occupied by locking screw 98) in top end 100 and a lower aperture (shown occupied by pedicle screw 58) in bottom end 102. Although not shown, the bottom end 102 includes an annular groove that is sized to receive a retaining ring (not shown) against which the head (not shown) of the pedicle screw 58 seats.

Receiver 62 includes a pair of upright branches 104, 106 that collectively define a U-shaped channel 108 transverse to the single opening defined longitudinally through the receiver. Moreover, the U-shaped channel 108 communicates with upper opening portion 62(*a*) and lower opening portion 62(*b*). The U-shaped channel 108 is sized to receive the proximal end 96 of spinal stabilization connector 54.

Locking cap 98 has a threaded body 110 that includes a series of threads that are compatible with internal threads (not shown) formed along the interior walls 112, 114 of branches 104, 106, respectively. In one embodiment, the internal threads of branches 104, 106 are reverse angle threads, such as disclosed in U.S. Pat. No. 6,296,242, the disclosure of which is incorporated herein by reference. It is understood, however, that the present disclosure is applicable with vertebral fasteners having other thread orientations. The branches 104, 106 also have indentations or holes 116, 118 that allow a surgeon to grip the receiver 62 with an appropriate gripping tool (not shown).

Vertebral fastener 52 also has a crown member 120 shaped to accommodate the head of pedicle screw 58. One exemplary crown member is more fully described in U.S. Pat. No. 6,280,442, the disclosure of which is incorporated herein by reference. Crown member 120 is constructed to fit within the lower opening portion 62(*b*) and compresses against the head of the pedicle screw 58 when the spinal stabilization connector 54 is secured within U-shaped channel 108.

Thus, once an appropriate hole is formed a vertebral member, pedicle screw 58, having been placed and secured within receiver 62, is inserted into the vertebral member. Once secured, the spinal stabilization connector 54 is placed within rod-receiving channel 108. Locking cap 98 is then threadingly connected to the receiver 62, in a manner similar to that described above. The locking cap 98 contacts against the proximal end 96 of the spinal stabilization connector 54, which causes the spinal stabilization connector 54 to push against crown member 120. Crown member 120 then compresses against the head of the pedicle screw 58 thereby locking fastener 52 and the spinal stabilization connector 54 into place. It is recognized that the spinal stabilization connector 54 may have a length greater than the distance between the fasteners 50, 52. As such, an appropriate cutting tool (not shown) may be used to cut-off lengths of the spinal stabilization connector 54 that extends distally past fastener 50 and proximally past fastener 52.

Figure 3:
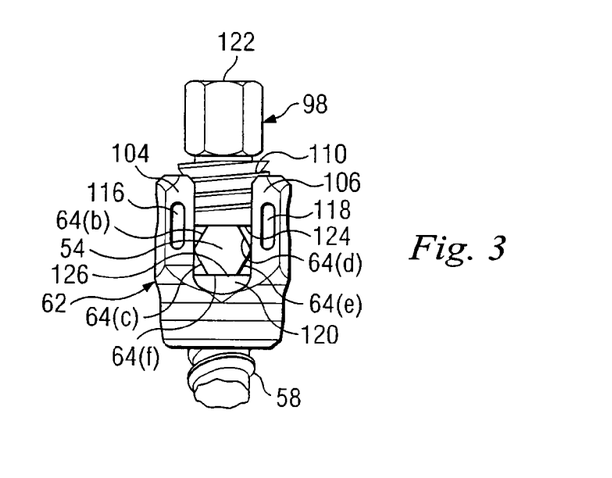
FIG. 3 is a partial end view of the vertebral stabilizing system according to one embodiment of the present disclosure.

Referring now to FIG. 3, an end view of vertebral fastener 52 illustrates one aspect of the present disclosure. As illustrated, the threaded body 110 of locking screw 98 has a proximal end 122 designed to engage an appropriate tool (not shown) for threading the locking screw 98 into the receiver 62. The distal end 124 of the locking screw 98 has a relatively planar surface that contacts a corresponding planar or flat surface 64(*a*) of the spinal stabilization connector 54. That is, as described above, in contrast to conventional round stabilizing rods, spinal stabilization connector 54 has a plurality of discretely defined and planar sidewalls that run along its length. Since the sidewalls have a planar exterior surface, a relatively planar or flat interface is provided for the distal end 124 of the locking screw. This provides a more force distributing interface than that provided by the tangential interface formed with the curved exterior surface of a conventional stabilizing rod.

Alternatively, the spinal stabilization connector can be constructed to have a groove defined along its length, or portion thereof, that is contoured to receive the distal end of the locking screw. In this arrangement, the groove in the connector provides a contoured seat for the locking screw. In another alternate embodiment, the crown member of each vertebral fastener can be constructed to have a groove or other geometry matched to the shape of the spinal stabilization connector. In this regard, the crown member is contoured to match the shape of the spinal stabilization connector and to thereby provide a seat for the spinal stabilization connector. For example, if the spinal stabilization connector is constructed to have a triangular cross-section, the crown member could be constructed to have a V-shaped groove appropriately contoured to receive the spinal stabilization connector.

In addition to providing a planar contact interface between the spinal stabilization connector 54 and the locking screw 98, the symmetry of the spinal stabilization connector 54 results in a planar interface with crown member 120. As shown in FIG. 3, the sidewall 64(*f*) opposite of sidewall 64(*a*) abuts the top surface 126 of crown member 120. As such, a force distributing interface is also formed between the spinal stabilization connector and the crown member. In one embodiment, the spinal stabilization connector has an equal number of planar sidewalls such that planar interfaces are formed between the spinal stabilization connector and the locking screw and between the spinal stabilization connector and the crown member, as described above. However, it is contemplated that the spinal stabilization connector could be constructed to have an odd number of planar sidewalls. With such a construction, it is preferred that a planar interface be formed between the spinal stabilization connector and the locking screw whereas a point interface is formed between the spinal stabilization connector and the crown member.

In addition to providing planar interfaces, the planar sidewalls of the spinal stabilization connector 54 define discrete positions of orientation for the spinal stabilization connector 54. As shown in FIG. 2, the spinal stabilization connector includes a curved portion 128 defined between the distal end 84 and the proximal end 96 that is offset from the line-of-sight axis defined between the vertebral fasteners. Moreover, in the illustrated example, the curved portion 128 extends along a plane that is 60 degrees offset from parallel vertical axes extending through the receivers.

Increasingly, spinal stabilization connectors are being manufactured to perform differently based on the orientation of the spinal stabilization connector relative to a spinal joint. In this regard, by constructing the spinal stabilization connector to have a plurality of discrete positions at which the spinal stabilization connector can be placed, optimal or preferred performance characteristics of the spinal stabilization connector can be readily achieved with appropriate placement of the spinal stabilization connector in the vertebral fasteners. In the case of the illustrated example, the spinal stabilization connector 54 can be placed at six discrete orientations based on the planar sidewall that is used to interface with the locking screw 98. Moreover, since the curvature is pre-defined along the length of the spinal stabilization connector 54, discrete angular positions of the curved portion 128 relative to the vertical axes can be similarly realized. That is, if it is desired for the curved portion 128 to be offset from the vertical axes by 240 degrees, than the spinal stabilization is rotated in such a manner to place planar sidewall 64(d) perpendicular to the vertical axes and thereby forming a planar interface between the planar sidewall 64(d) and the planar distal surface 124 of the locking screw 98. It is understood that the number of discrete positions can be more or less than the six positions defined by the spinal stabilization connector 54 illustrated in FIGS. 1-3. Moreover, the curved portion of the spinal stabilization connector can be constructed to have other geometries than those described above, as will be described with respect to FIGS. 7a-9b.

FIGS. 4a-9b illustrate spinal stabilization connectors according to alternate embodiments of the present disclosure. In some of the figures, the spinal stabilization connectors are shown connected to a single fastener. However, it is understood that in practice, the spinal stabilization connectors would be connected to at least two vertebral fasteners to provide spinal stabilization. Also, in describing the spinal stabilization connectors of FIGS. 4a-9b, various features of the vertebral stabilizer will be referenced. These features, as well as additional features not described with respect to FIGS. 4a-9b are described and illustrated in FIGS. 1-3. Therefore, unless otherwise noted, the vertebral fasteners described in FIGS. 4a-9b are similar in construction to the vertebral fasteners described in FIGS. 1-3. Additionally, reference will be made to the spinal stabilization connectors being fastened to vertebral fastener 52 in the description of FIGS. 4a-9b, but it is understood that the spinal stabilization connectors would fasten in a similar manner to vertebral fastener 54 described in FIGS. 1-3. Also, where appropriate, parts illustrated in FIGS. 4a-9b will be referenced with like numbers as corresponding parts illustrated in and described with respect to FIGS. 1-3.

Figures 4A, 4B, 4C:
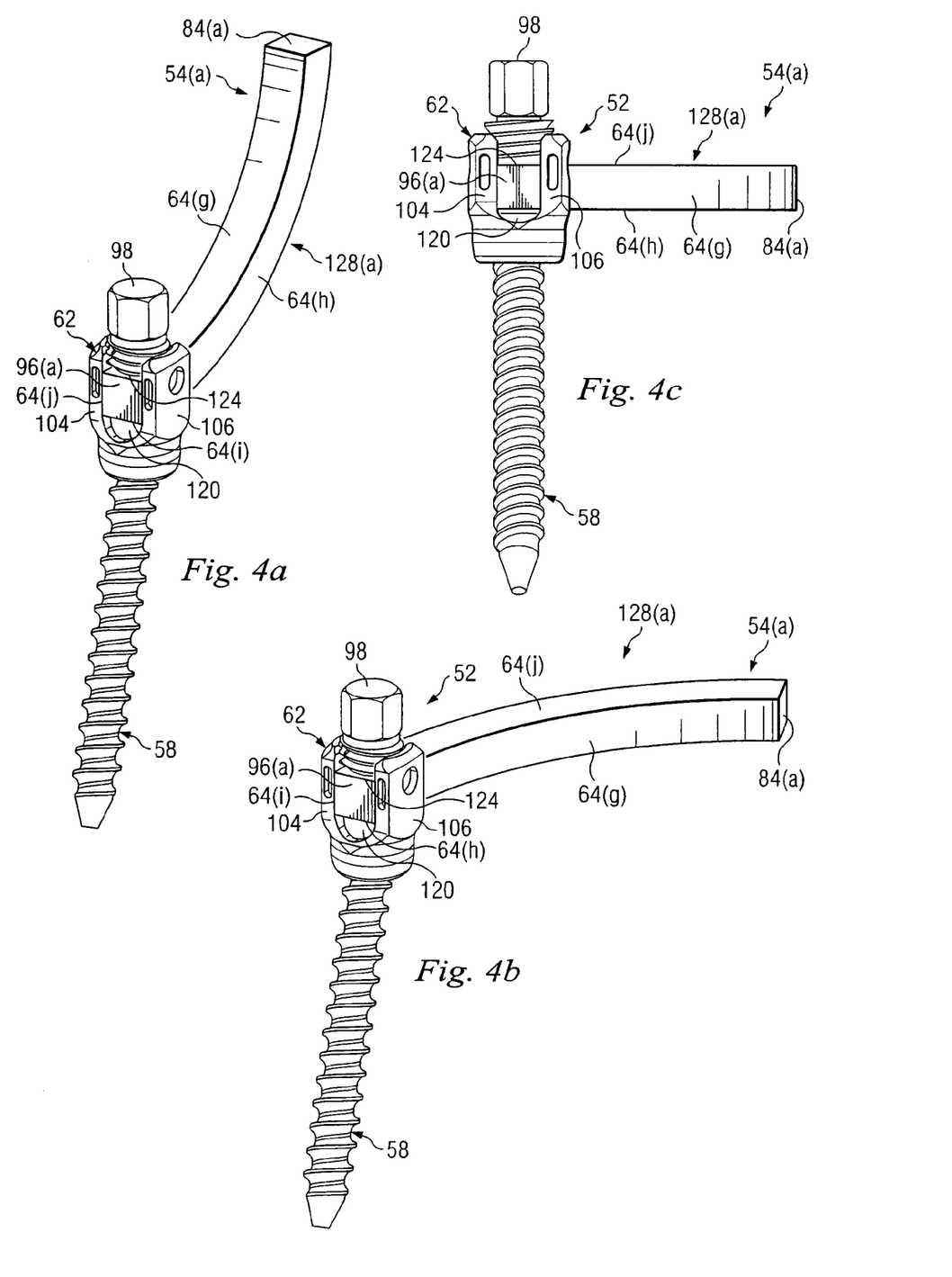
FIGS. 4a-4c are partial perspective views of the vertebral stabilizing system illustrating various orientation positions for a spinal stabilization connector according to one embodiment of the present disclosure.

FIGS. 4a-4c illustrate a spinal stabilization connector 54(a) constructed to have four equally sized sidewalls 64(g), 64(h), 64(i), 64(j), i.e., a square cross-section. The spinal stabilization connector 54(a) is shown connected at one end to vertebral fastener 52. Specifically, FIG. 4a shows the spinal stabilization connector 54(a) connected to the vertebral fastener 52 such that the curved portion 128(a) is oriented to not be offset from the vertical axes extending through the vertebral fastener 52. However, because of the defined curvature, the spinal stabilization connector 54(a) has a relatively concave shape between ends 84(a) and 96(a). If the spinal stabilization connector 54(a) was rotated 180 degrees from the position shown in FIG. 4a, the spinal stabilization connector 54(a) would have a relative convex shape defined between ends 84(a) and 96(a). FIG. 4b illustrates the orientation of the spinal stabilization connector 54(a) relative to vertebral member 52 if the spinal stabilization connector 54(a) is rotated 90 degrees to the right from the orientation shown in FIG. 4a. It is noted that in both orientations, a planar interface is formed between the distal planar surface 124 of the locking screw 98 and a planar sidewall of the spinal stabilization connector 54(a). Specifically, in FIG. 4a, the distal planar surface 124 of the locking screw 98 abuts against planar sidewall 64(g) whereas in FIG. 4b, the distal planar surface 124 abuts against planar sidewall 64(j). FIG. 4c is a an end view of that shown in FIG. 4b, which illustrates the curvature of the spinal stabilization connector 54(a) as being offset from the line-of-sight axis that extends through the vertebral fastener 52 along the rod-receiving channel. It is noted that the present disclosure includes spinal stabilization connectors having more or less than four sidewalls.

Figures 5A, 5B:
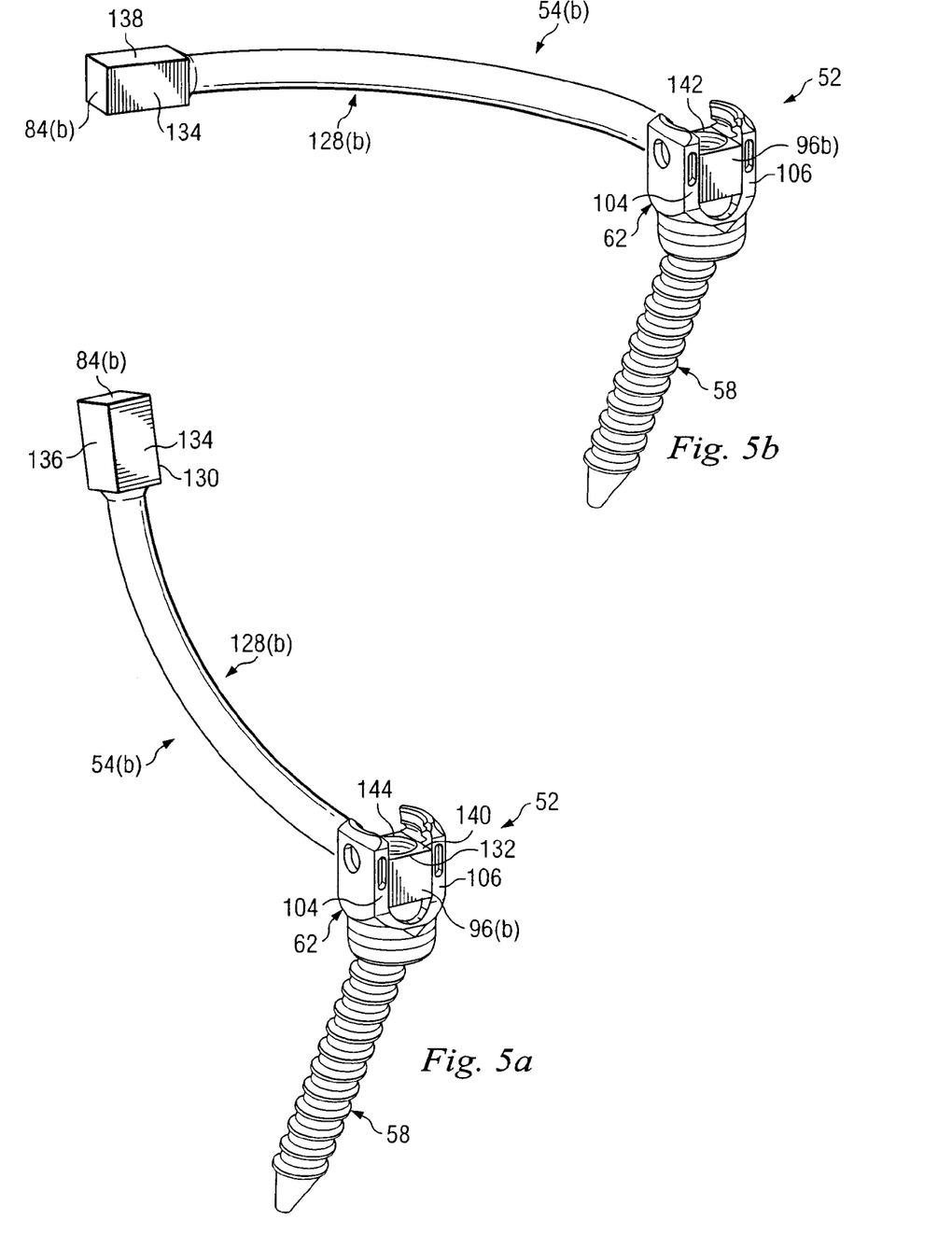
FIGS. 5a-5b are perspective views of another vertebral stabilizing system illustrating various orientation positions for a spinal stabilization connector according to another embodiment of the present disclosure.

FIGS. 5a and 5b illustrate a spinal stabilization connector 54(b) according to another embodiment of the present disclosure. Spinal stabilization connector 54(b) has a curved portion 128(b) with a circular cross-section with ends 84(b) and 96(b) each having a multi-sided boss 130, 132, respectively. In the illustrated embodiment, boss 130 has four planar sidewalls, of which sidewalls 134, 136, and 138 are shown. Similarly, boss 132 has four planar sidewalls, of which sidewalls 140 and 142 are shown. In one embodiment, bosses 130, 132 are integrally formed with curved portion 128(b). Alternately, the bosses may be separately formed and connected using adhesive or other mechanical connections, such as twist-lock or threaded engagements. Similar to the spinal stabilization connectors described above, the sidewalls of bosses 130, 132 define discrete positions at which the spinal stabilization connector 54(b) can be oriented relative to a spinal joint. In FIG. 5a, the spinal stabilization connector 54(b) is placed in the vertebral fastener 52 such that sidewall 140 of boss 132 and sidewall 134 of boss 130 are perpendicular to the vertical axis that extends through the vertebral fastener. FIG. 5b shows the position of the spinal stabilization connector 54(b) having been rotated 90 degrees to the left. As such, sidewalls 134, 140 are parallel to the vertical axes that extends through the vertebral fastener 52.

Also, FIGS. 5a and 5b illustrate the vertebral fastener 52 with the locking screw 98 removed. As such, the internal threads 144 of branch 106 are shown. Branch 104 similarly has internal threads (not shown). As described above, these internal threads engage the threaded body of the locking screw when the locking screw is fastened to the receiver 62. Additionally, while the spinal stabilization connector is shown as having two bosses, one at each end; it is noted that the spinal stabilization connector may be constructed to have more than two bosses formed along its length. Also, a spinal stabilization connector may have bosses of different sizes. For example, the spinal stabilization connector may have one boss to accommodate a single screw and have another, but longer, boss sized to accommodate multiple screws.

Figure 6A:
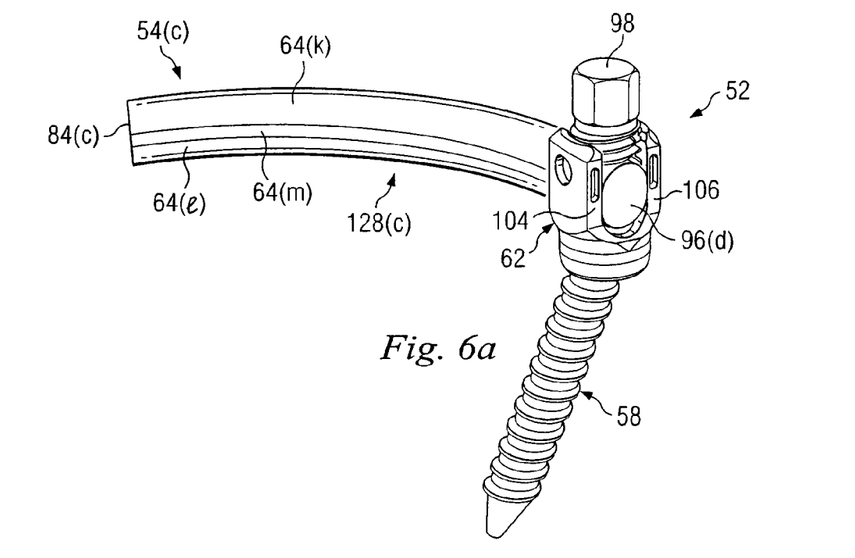
FIGS. 6a-6c are perspective views of yet another vertebral stabilizing system illustrating various orientation positions for a spinal stabilization connector according to yet another embodiment of the present disclosure.
Figures 6B, 6C:
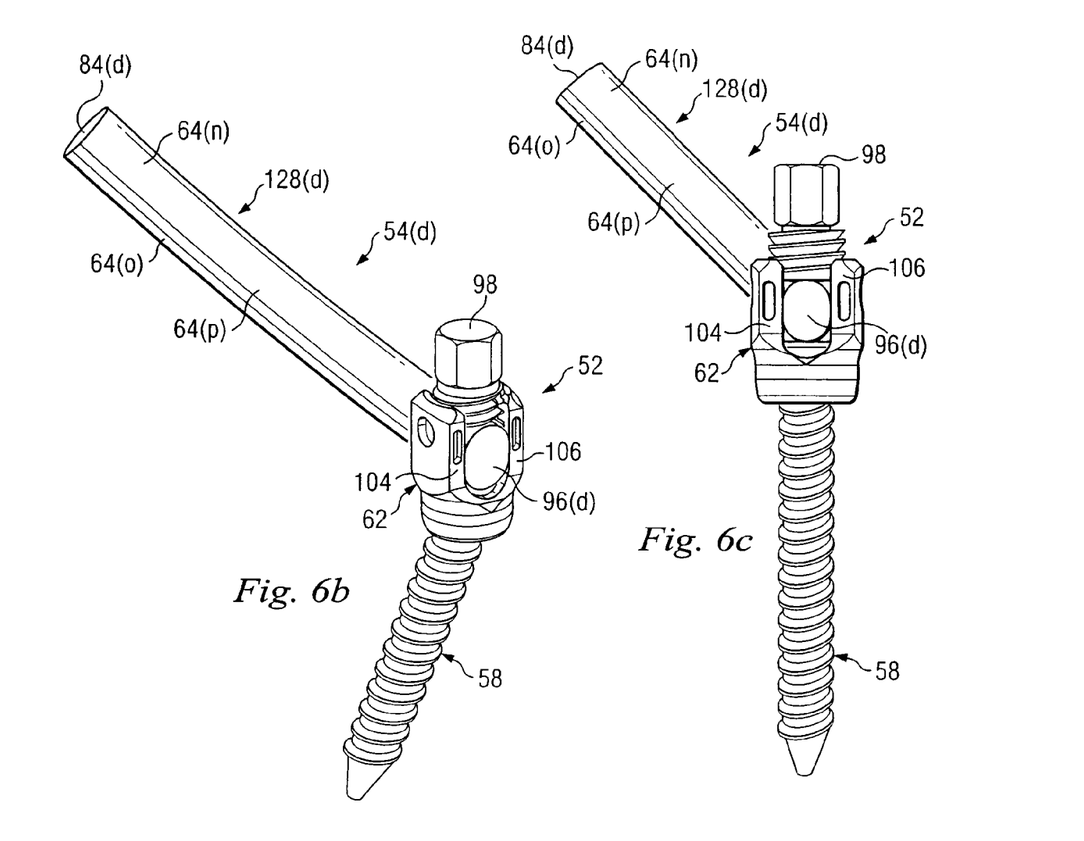

FIGS. 6a-6c illustrated spinal stabilization connectors according to additional aspects of the present disclosure. The spinal stabilization connectors illustrated in FIGS. 6a-6c have oval-shaped cross-sections. For example, spinal stabilization connector 54(c) has a curved portion 128(c) defined between ends 84(c) and 96(c). The curved portion 128(c) is defined by a pair of facing arcuate sidewalls 64(k), 64(l). The arcuate sidewalls are joined together by a pair of facing planar sidewalls, of which sidewall 64(m) is shown. The pair of planar sidewalls define two discrete positions of orientation for spinal stabilization connector 54(c). The two discrete positions are rotated 180 degrees from one another such that spinal stabilization connector 54(c) can be placed in the vertebral fastener so that the curved extends to the left in the figure or to the right in the figure.

Contrastingly, the spinal stabilization connector 54(d) illustrated in FIGS. 6b and 6c, which also is shaped to have an oval cross-section, defines a pair of discrete positions that result in curved portion 128(d) pointing upward in the figure or pointing downward in the figure. That is, in FIGS. 6b and 6c, the spinal stabilization connector 54(d) is placed in the vertebral fastener 52 so that the curved portion is concave between ends 84(d) and 96(d). Rotating the spinal stabilization connector 54(d) by 180 degrees, for example, would result in the curved portion having a convex orientation between ends 84(d) and 96(d). It is recognized that the direction of curvature of the spinal stabilization connectors illustrated in FIGS. 6a-6c can be changed by changing the relative position of the planar sidewalls relative to the arcuate sidewalls. That is, the spinal stabilization connector may be constructed such that the angular displacement between the pair of discrete positions is less than (or more than) 180 degrees.

Figure 7A:
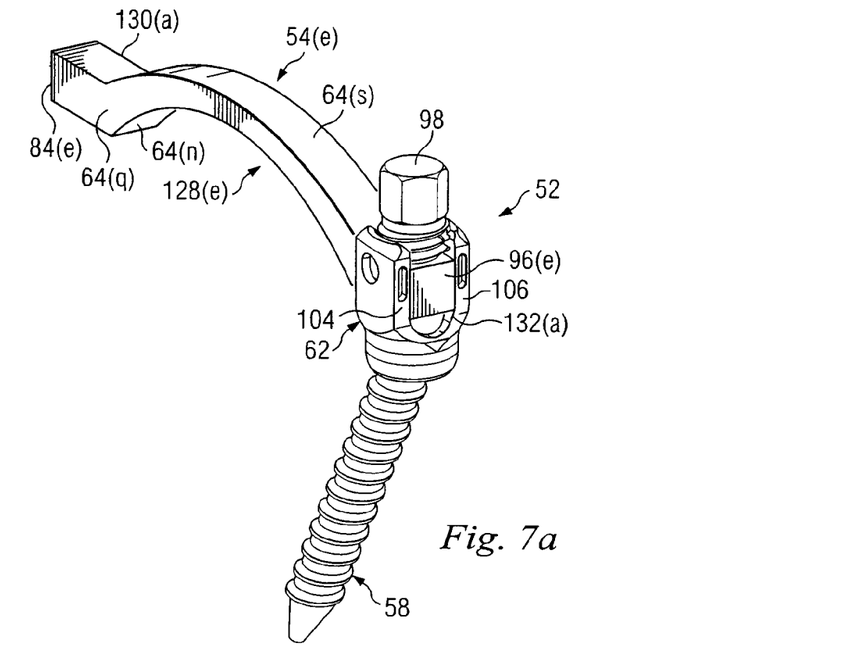
FIGS. 7a-7b are perspective views of another vertebral stabilizing system illustrating various orientation positions for a spinal stabilization connector according to another embodiment of the present disclosure.

FIGS. 7a-9b illustrate spinal stabilization connectors according to another aspect of the invention. As will be described, the spinal stabilization connectors illustrated in FIGS. 7a-9b have a curved portion shaped as a ribbon feature disposed between bosses at respective ends of a spinal stabilization connector. For example, spinal stabilization connector 54(e), as shown in FIGS. 7a and 7b, has a pair of bosses 130(a),132(b) at ends 84(e), 96(e), respectively. A curved portion 128(e) extends between the pair of bosses 130(a), 132(a) and is shaped as a ribbon feature. In the illustrated example, the spinal stabilization connector 54(e) is a four-sided connector with a pair of planar sidewalls that run along the entire length of the spinal stabilization connector 54(e), of which sidewall 64(q) is shown. Opposite the planar sidewalls are non-planar sidewalls, of which sidewalls 64(r), 64(s), are shown. Sidewalls 64(r), 64(s) are not entirely planar along their length as a result of the ribbon feature. However, as the ribbon feature does not extend to ends 84(e), 96(e), the bosses 130(a), 132(a) are defined by four planar surfaces. Thus, in a manner similar to that described with respect to FIGS. 5a and 5b, the spinal stabilization connector 54(e) can be oriented at one of four discrete positions of orientation. One such position is shown in FIG. 7a. Another position, rotated ninety degrees from that shown in FIG. 7a, is illustrated in FIG. 7b. In both positions, as well as the other two possible orientations not shown, a planar interface is formed between the spinal stabilization connector 54(e) and the locking screw 98.

Figure 7B:
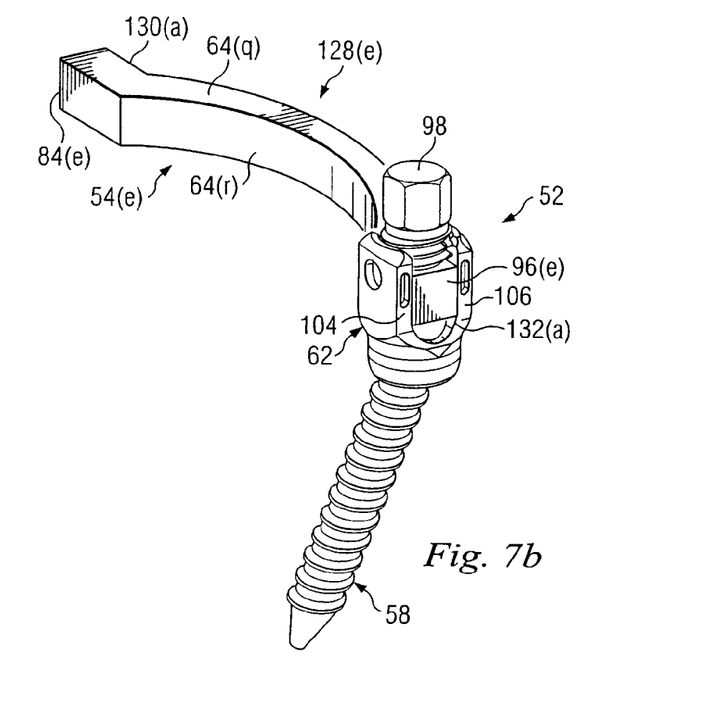
Figures 8, 9A:
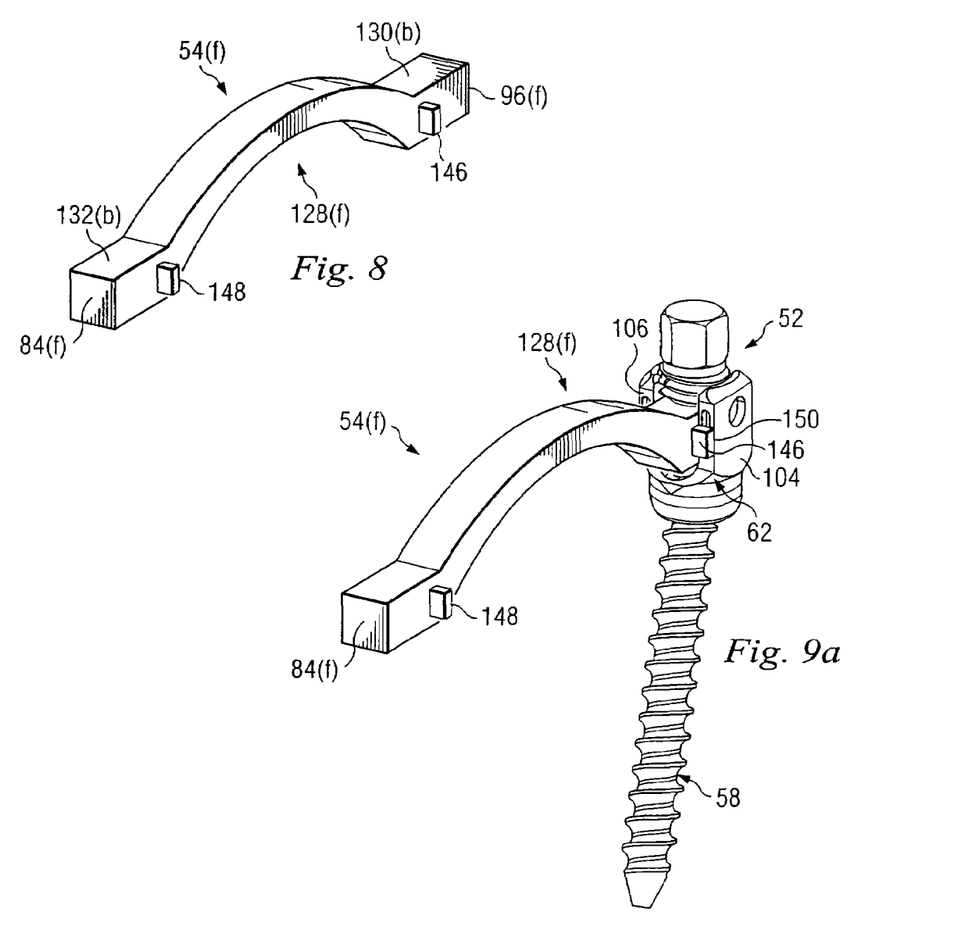
FIG. 8 is a perspective view of a spinal stabilization connector according to another embodiment of the present disclosure.
FIG. 9a is a perspective view of the spinal stabilization connector of FIG. 8 with one end secured within a receiver according to one embodiment of the present disclosure.
Figure 9B:
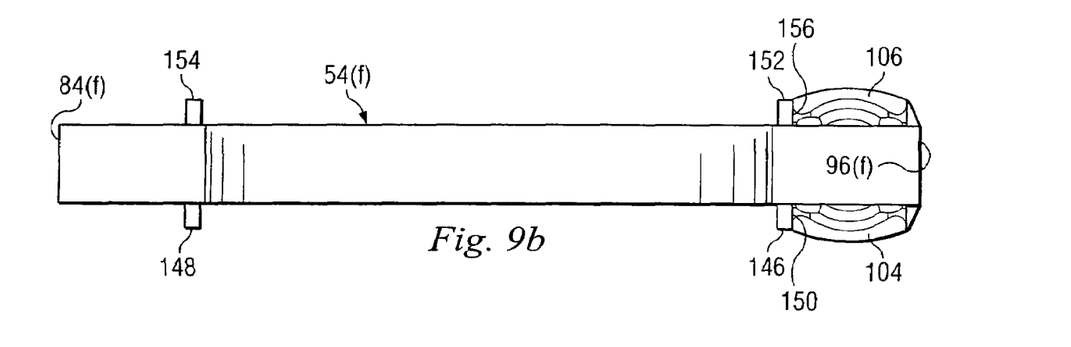

FIGS. 8 through 9b illustrate a spinal stabilization connector 54(f) incorporating translational stops. While the translational stops are illustrated with respect to a spinal stabilization connector similar to that illustrated in FIGS. 7a through 7b, it is understood that the other spinal stabilization connectors described herein, or equivalents thereof, may also be constructed to have translational stops.

Spinal stabilization connector 54(f) is similar to the spinal stabilization connector illustrated in FIGS. 7a and 7b with the addition of flanges 146, 148 that extend from bosses 130(b), 132(b), respectively. Flanges 146, 148 operate as translational stops thereby limiting the translational movement of the spinal stabilization connector 54(f) relative to the vertebral fasteners. More particularly, the spinal stabilization connector 54(f) may be constructed to have an optimal or preferred distance between vertebral fasteners. The flanges 146, 148 define that distance. As such, when a surgeon is implanting the vertebral fasteners, the distance between the vertebral fasteners should be such that the flanges 146, 148 rest against or abut the face of respective receivers, as illustrated in FIG. 9a, for example. As shown in FIG. 9a, when the spinal stabilization connector 54(f) is properly placed in the receiver 62, flange 146 abuts against the face 150 of branch 104. As shown in FIG. 9b, in one embodiment, spinal stabilization connector 54(f) has a total of four flanges 146, 148, 152, 154, two positioned at each of the bosses 130(b), 132(b). As such, flanges 146, 152 will abut against receiver 62. Specifically, flange 146 abuts face 150 of branch 104 and flange 152 abuts face 156 of branch 106. Flanges 148, 154 will similarly abut against faces of receiver 60 when the spinal stabilization connector 54(f) is placed therein. It is contemplated that the spinal stabilization connector could be constructed to have less than or more than four flanges.

The spinal stabilization connectors shown in FIGS. 7a-9b have a curved portion shaped as a ribbon feature. It is noted that the ribbon feature illustrates one exemplary geometry contemplated for the curved portion of the spinal stabilization connector. In this regard, it is contemplated that the curved portion may have other geometries or shapes different from those shown in the figures. Moreover, is contemplated that the curved portions may be vertically offset from the ends or bosses of the respective spinal stabilization connectors described herein. That is, in the example of FIGS. 7a-9b, the connectors may be constructed to include a riser (not shown) connected or otherwise extending from each of the bosses. The riser vertically offsets the curved portion from the bosses by the height of the risers. It is noted that the risers could be integrally formed with the bosses, e.g. L-shaped bosses, or may mechanically affixed to the bosses using a known or to be developed affixation technique.

The spinal stabilization connectors described herein may be placed directly adjacent the vertebrae, or alternatively, may be spaced from the vertebrae. In some embodiments, placement of the spinal stabilization connector directly adjacent the vertebrae may impart specific characteristics to the spinal stabilization connector. In some examples, the spinal stabilization connector may be spaced from the vertebrae. Accordingly even when the vertebral column is in flexion, causing the spine to bend forward, the vertebral fasteners maintain a line of sight position, so that the spinal stabilization connector extends only along a single axis, without bending. In other examples, after placement, the spinal stabilization connector may contact portions of the vertebrae during the flexion process. For example, during flexion, the vertebrae may move so that the first and second vertebral fasteners do not have a line of sight position. Accordingly, the spinal stabilization connector may be forced to bend around a protruding portion of the vertebrae. This may impart additional characteristics to the spinal stabilization connector. For example, because the spinal stabilization connector would effectively contact the spinal column at three locations (its two ends and somewhere between the two ends), its resistance to extension might be increased.

In the exemplary embodiments described, the spinal stabilization connector is the only component extending from one vertebral fastener to the other. This may be referred to as a single spinal stabilization connector. This single spinal stabilization connector may be contrasted with conventional systems that employ more than one connector extending between attachment points, such as systems with one component connected at the attachment points and another component extending between attachment points. Because it employs a single spinal stabilization connector, the vertebral stabilizing system disclosed herein may be easier and quicker to install, may be less complex, and may be more reliable than prior devices.

It should be noted however, that a spinal column may employ the spinal stabilization connector to extend across a first vertebral space, with a second spinal stabilization connector extending across a second vertebral space. Accordingly, more than one vertebral stabilizing system may be used in a spinal column. In some instances where more than one stabilizing system is use, the first and second vertebral spaces may be adjacent. In alternative embodiments, a vertebral stabilizing system may have a single spinal stabilization connector with a length allowing it to extend across more than one intervertebral space, with or without connecting to an intermediate vertebra.

Additionally, it is noted that a spinal stabilization connector can have a length that spans multiple spinal joints and, if necessary, more than two vertebral fasteners may be used to secure the spinal stabilization connector to vertebral members. Moreover, while the figures have been described with respect to placement of vertebral fasteners at the ends of a spinal stabilization connector, it is noted that vertebral fasteners could be placed at any position along the length of the spinal stabilization connector as deemed appropriate. It also noted that in the figures above, the geometry of the curved portion of a spinal stabilization connector is shown as being uniform in shape and size; however, it is contemplated that the spinal stabilization connector can have a variability in size and geometry along its length. For example, the spinal stabilization connector could be tapered from one end to the other or have multiple geometries defined along its length. In another example, spinal stabilization across multiple spinal joints is provided by using multiple spinal stabilization systems connected to one another. In this regard, it is contemplated that multiple spinal stabilization connectors can extend along the spinal column. Moreover, it is contemplated that the geometry (or size) of the spinal stabilization connectors used to provide spinal stabilization may vary along the length of the spinal column.

Also, a spinal stabilization connector has been described and shown as having planar sidewalls extending along its length. It is contemplated that the spinal stabilization connector could be constructed to have "soft" or slightly curved joints formed between the generally planar sidewalls rather than the "hard" joints shown in the figures. Further, the spinal stabilization connectors have been described and shown as having ends that are similarly shaped. However, it is contemplated that a spinal stabilization connector may have one end (or fastening position) with a first geometry and may have another end (or other fastening position) with a second geometry, different from the first geometry. Additionally, the present disclosure has been described with respect to various threaded engagements; however, it is understood that other types of engagements could be used, such as twist-locks, quarter-turn or half-turn locks, straps, clamps, and the like.

In certain anatomies, the vertebral stabilizing system may be used alone to provide decompression or compression to a single targeted facet joint or to relieve pressure on a particular side of the intervertebral disc, such as a herniation area. However, in some instances, a second vertebral stabilizing system may be installed on the opposite lateral side of the vertebrae across from the vertebral stabilizing system. Use of first and second vertebral stabilizing systems may provide more balanced support and equalized stabilization. The second vertebral stabilizing system may be substantially similar to system and therefore will not be described in detail.

The vertebral stabilizing system, as installed, may flexibly restrict over-compression of the vertebrae, thereby relieving pressure on the intervertebral disc and the facet joint. In addition, the vertebral stabilizing system may flexibly restrict axial over-extension of the intervertebral disc and the facet joint. By controlling both compression and extension, the vertebral stabilizing system may reduce wear and further degeneration. The spinal stabilization connector may also dampen the forces on the intervertebral disc and facet joint during motion such as flexion and extension. Because the spinal stabilization connector may be positioned relatively close to the natural axis of flexion, the vertebral stabilizing system may be less likely to induce kyphosis as compared to systems that rely upon inter-spinous process devices to provide compressive and tensile support. Additionally, the system may be installed minimally invasively with less dissection than the inter-spinous process devices of the prior art. Furthermore, an inter-pedicular system can be used on each lateral side of the vertebrae, and may provide greater and more balanced stabilization than single inter-spinous process devices.

It should be noted that in some embodiments, the spinal stabilization connector may be configured so that orientation in one direction provides one set of stabilizing properties to the vertebrae, while orienting the spinal stabilization connector in the other direction would provide a second set of stabilizing properties. Also, while the figures have been described with respect to a spinal stabilization rod, it is understood that the present disclosure is applicable with other types of connectors or tension members such as spinal stabilization plates.

It should be noted that the spinal stabilization connector can be made of elastic or semi-elastic materials in parts or in its entirety. On the other hand, the spinal stabilization connector can be made of a composite of elastic/semi-elastic and inelastic or rigid materials, such as that described in U.S. Ser. No. 11/7413,448, the disclosure of which is incorporated herein by reference. Exemplary elastic materials include polyurethane, silicone, silicone-polyurethane, polyolefin rubbers, hydrogels, and the like. The elastic materials can be resorbable, semi-resorbable, or non-resorbable. Exemplary inelastic materials include polymers, such as polyetheretherketone (PEEK), polyetherketoneketone (PEKK), and polylactic acid materials (PLA and PLDLA), metals, such as titanium, NITINOL, and stainless steel, and/or ceramics, such as calcium phosphate and alumina. Further, the various connector components can be solid, hollow, semi-hollow, braided, woven, mesh, porous, or combinations thereof. The connector can also be reinforced or semi-reinforced. Additionally, the connector can be made to have a variable rigidity, such as that described in U.S. Ser. No. 11/563,594, the disclosure of which is incorporated herein by reference. It is also contemplated that the connector can be fabricated using a number of fabrication techniques, such as injection molding as described in U.S. Ser. No. 11/469,354, the disclosure of which is incorporated herein by reference. Also, in one embodiment, the width between the planar sidewalls is equal to the diameter of conventional round spinal stabilization connectors; however, it is contemplated the distance between the planar sidewalls could be more or less than the diameter of conventional round spinal stabilization rounds. Therefore, it is also contemplated that the vertebral fasteners could be constructed to have a wider or narrow rod-receiving channel to accommodate the width of the spinal stabilization connectors described herein. Also, the spinal stabilization connectors may have different cross-sectional shapes than those shown and described. For example, the spinal stabilization connector could be constructed to have a D-shaped cross-section.

Although disclosed as being used at the posterior areas of the spine, the spinal stabilization connector may also be used in the anterior region of the spine to support the anterior column. In such a use, the spinal stabilization connector may be oriented adjacent to and connect to the anterior column, and may span a vertebral disc space.

The foregoing embodiments of the stabilization system may be provided individually or in a kit providing a variety of sizes of components as well as a variety of strengths for the connector. It is also contemplated that the connector's characteristics may be color coded or otherwise indicated on the connector itself to expedite identification of a desired connector.

The invention is also embodied in a surgical method for spinal or other bone stabilization. In accordance with this method, a surgeon performs a conventional interbody fusion/nucleus replacement/disc replacement followed by placement of pedicles/bone screws or other inserters into appropriate vertebral or other bony structures. The surgeon may then anchor one end of a connector into a first vertebral or other bony structure. If necessary or otherwise desired, tension is applied to the connector spanning the space between bony structures. The un-anchored end of the connector is then anchored to a second vertebral or other bony structure spaced from the first vertebral or other bony structure.

It is noted that various embodiments of the spinal stabilization connector described herein may include disjointed sections that can be threadingly engaged or otherwise connected to each other on a per patient basis. Thus, the above surgical method contemplates a surgeon connecting segments to each other until a desired length, elasticity, and the like is achieved. Moreover, a surgeon can construct such a connector on-the-fly quickly and with relative ease by connecting segments or components to one another.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. Further, the embodiments of the present disclosure may be adapted to work singly or in combination over multiple spinal levels and vertebral motion segments. Also, though the embodiments have been described with respect to the spine and, more particularly, to vertebral motion segments, the present disclosure has similar application to other motion segments and parts of the body. In the claims, means-plus-function clauses are intended to cover the elements described herein as performing the recited function and not only structural equivalents, but also equivalent elements.

What is claimed is:

1. A spinal stabilizing system comprising:
   a spinal stabilization connector designed to traverse a space between a pair of vertebral members, the spinal stabilization connector including:
      first and second ends having respective longitudinal axes and each having at least three planar sidewall surfaces extending between vertices, the vertices parallel to the longitudinal axis at each of the first and second ends, the at least three planar sidewall surfaces defining a plurality of discrete positions for the spinal stabilization connector relative to the vertebral members, the first and second ends each having a maximum diameter as measured between at least two of the vertices, and
      a body connected to the first and second ends, the body having a curved portion extending between the first and second ends;
   a receiver having a channel extending along a channel longitudinal axis for receiving one of the first and second ends, an opening into the channel having a width equal to the maximum diameter of one of the first and second ends, the width of the opening being substantially transverse to the channel longitudinal axis, the channel being sized such that the first and second ends are rotatable about their respective longitudinal axes within the channel such that the rotation changes a path of traversal of the curved portion across the space between the pair of vertebral members; and
   a crown member disposed within the receiver and having a planar surface defining a bottom surface of the channel, the planar surface extending at least the width of the opening and substantially transverse to the channel longitudinal axis such that one of the sidewall surfaces interfaces with the planar surface in a manner that distributes forces applied to the planar surface by the spinal stabilization connector.

2. The spinal stabilizing system of claim 1 wherein the plurality of discrete positions are equal in number to the plurality of sidewalls.

3. The spinal stabilizing system of claim 2 wherein each of the first and second ends has sidewalls of equal size.

4. The spinal stabilizing system of claim 3 wherein each of the first and second ends has four planar sidewall surface.

5. The spinal stabilizing system of claim 3 wherein each of the first and second ends has six planar sidewall surface.

6. The spinal stabilizing system of claim 2 wherein the body includes planar sidewall surfaces equal in number to the planar sidewall surfaces of the first and second ends, and wherein the sidewall surfaces of the body are linearly aligned with the of sidewall surfaces of the first and second ends.

7. The spinal stabilizing system of claim 1 further comprising:
   a screw having a shank designed to engage a vertebral member and a head designed to be received by the receiver; and a set screw designed to abut at least one of the planar sidewall surfaces of an end of the spinal stabilization connector to lock the spinal stabilization connector in the receiver.

8. The spinal stabilizing system of claim 7 wherein the set screw has a relatively planar distal end that abuts the at least one of the planar sidewall surface of the end of the spinal stabilization connector.

9. The spinal stabilizing system of claim 7 wherein the rod-receiving channel is contoured to match a contour of an end of the spinal stabilization connector.

10. A spinal stabilizing kit comprising:
   a pair of bone-engaging screws, each bone-engaging screw retainable by a receiver and drivingly engageable with a bony structure;
   the spinal stabilization connector retainable by a pair of receivers and designed to traverse a space between a pair of vertebral members, the spinal stabilization connector having a substantially curved portion and first and second ends spaced from one another by the substantially curved portion, the first and second ends having respective longitudinal axes and each having at least three planar sidewall surfaces extending between vertices, the vertices parallel to the longitudinal axis at each of the first and second ends, the at least three planar sidewall surfaces defining a discrete number of positions at which the spinal stabilization connector may be retained by the pair of receivers, the first and second ends each having a maximum diameter as measured between at least two of the vertices;
   a pair of locking screws, each locking screw designed to lock the spinal stabilization connector in the pair of receivers;
   the pair of receivers each having a channel extending along respective channel longitudinal axes for receiving one of the first and second ends, an opening into each channel having a width equal to the maximum diameter of one of the first and second ends, the width of each opening being substantially transverse to the respective channel longitudinal axes, each channel being sized such that the first and second ends are rotatable about their respective longitudinal axes within the channel such that the rotation changes a path of traversal of the curved portion across the space between the pair of vertebral members; and
   a crown member disposed within each receiver and each crown member having a planar surface defining a bottom surface of each channel, each planar surface extending at least the width of each opening and substantially transverse to the respective channel longitudinal axes such that one of the sidewall surfaces interfaces with the planar surface in a manner that distributes forces applied to the planar surface by the spinal stabilization connector.

11. The spinal stabilization kit of claim 10 wherein the at least three planar sidewall surfaces of the first and second ends define more than two discrete positions along each of the at least three planar sidewall surfaces at which the spinal stabilization connector may be retained by the pair of receivers.

12. The spinal stabilization kit of claim 10 wherein the discrete number of positions define rotational stabilization positions at which the spinal stabilization connector can be oriented relative to a spinal joint.

13. The spinal stabilization kit of claim 10 wherein the first and second ends are shaped to define at least six discrete positions at which the spinal stabilization connector may be retained by the pair of receivers.

14. The spinal stabilization kit of claim 10 wherein the spinal stabilization connector has one of a square, a hexagonal, or an oval shaped cross-section.

15. The spinal stabilization kit of claim 10 wherein the pair of receivers, the pair of bone-engaging screws, the spinal stabilization connector, and the pair of locking screws are comprised of bio-compatible material.

16. The spinal stabilization kit of claim 10 wherein the spinal stabilization connector is configured to flex in a first direction and restrict movement in a second direction opposite the first direction.

17. The spinal stabilization kit of claim 10 wherein the spinal stabilization connector is comprised of PEEK.

18. The spinal stabilization kit of claim 10 wherein the at least three planar sidewall surfaces of the first and second ends define a perimeter of the first and second ends about their respective longitudinal axes.

19. The spinal stabilization kit of claim 18 wherein each locking screw has a threaded body having a proximal end and a distal end, wherein the proximal end has a surface designed to receive a driving tool for threadingly fastening the locking screw to one of the receivers and the distal end has a relatively planar surface designed to engage, in a force-distributing manner, one of the planar sidewall surfaces of the spinal stabilization connector when the spinal stabilization connector is retained in the receiver.

20. The spinal stabilization kit of claim 10 wherein the channel is shaped to match a contour of a respective end of the spinal stabilization connector.

21. The spinal stabilization kit of claim 10 wherein the first and second ends are formed of a first material and the substantially curved portion is formed of a second material, different from the first material.

* * * * *